US00PP14129P3

(12) United States Plant Patent

Anderson et al.

(10) Patent No.: US PP14,129 P3

(45) Date of Patent: Sep. 2, 2003

(54) CHRYSANTHEMUM PLANT NAMED 'MN95-105-6'

(75) Inventors: Neil Owen Anderson, St. Paul, MN (US); Peter David Ascher, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/503,578

(22) Filed: Feb. 14, 2000

(65) Prior Publication Data

US 2003/0126660 P1 Jul. 3, 2003

(51) Int. Cl.[7] ..... A01H 5/00

(52) U.S. Cl. ..... Plt./284

(58) Field of Search ..... Plt./284, 286, 291

(56) References Cited

U.S. PATENT DOCUMENTS

| | | | |
|---|---|---|---|
| PP7,513 | P | 4/1991 | VandenBerg |
| PP7,754 | P | 12/1991 | VandenBerg |
| PP8,759 | P | 5/1994 | VandenBerg |
| PP8,987 | P | 11/1994 | VandenBerg |
| PP9,445 | P | 1/1996 | VandenBerg |
| PP9,578 | P | 6/1996 | Fuess |
| PP10,848 | P | 4/1999 | VandenBerg |
| PP10,909 | P | 5/1999 | Wain |
| PP10,943 | P | 6/1999 | Fuess |
| PP11,009 | P | 7/1999 | Davino, Jr. |
| PP11,032 | P | 8/1999 | Glicenstein |

OTHER PUBLICATIONS

Wilson, Robert, Horticultural Colour Chart, The British Colour Council, 1941, p. 175.*

Peter Ascher, et al., Maxi-Mums A Horticulural Breakthrough!, Minnesota Report 242-1997 University of Minnesota, Distribution Center Publication MR-67280B Minnesota Agricultural Experiment Station University of Minnesota (1997).

R.B. Clark, History of Culture of Hardy Chrysanthemums, National Chrysanthemum Society 18(3):144, 1962.

W.W. Garner, et al., Flowering and Fruiting of Plants as Controlled By The Length Of Day, 1920, p. 377–400, Yearbook of the Department of Agriculture, 1920, USA.

Peter Ascher, et al., Breeding and New Cultivars, Academic Perspective, Tips on Growing and Marketing Garden Mums, Ohio Florist's Association 1996.

Bradford Bearce, et al., Chrysanthemums A Manual of the Culture, Diseases, Insects and Ecocomics of Chrysanthemums, Jun. 1964, pp. 6–19, Prepared for The New York State Extension Service Chrysanthemum School with the Cooperation of the New York State Flower Growers Association, Inc.

Neil O. Anderson, et al., Rapid Generation Cycling of Chrysanthemum Using Laboratory Seed Development and Embryo Rescue Techniques, Journal of the American Society of Horticultural Science, Mar. 1990, pp. 329–336, vol. 115(2), Alexandria, Virginia 22314.

Leon Glicenstein, Breeding and New Cultivars, Commercial Perspective, Tips on Growing and Marketing Garden Mums, Ohio Florist's Association 1996.

M.A. Nazeer, et al., Cytyogenetical Evolution of Garden Chrysanthemum, Current Science, Jun. 20, 1982, vol. 51, No. 12.

Edward Higgins, Containers and Marketing, Tips on Growing and Marketing Garden Mums, Ohio Florist's Association 1996.

Naomasa Shimotomai, Bastardierungsversuche bei Chrysanthemum I., Journal of Science of the Hiroshima University, Series, B, Div. 2, vol. 1, Art. 3, 1931.

Naomasa Shimotomai, Bastardierungsversuche bei Chrysanthemum II. Eentstehung eines fruchtbaren Bastardes (haploid $4n^2$) aus der Kreuzung von Ch. marginatum (hapl. 5n) mit *Ch. morifolium* (hapl. 3n), Journal of Science of the Hiroshima University, Series B, Div. 2, vol. 1, Art. 8, 1932.

Ernest L. Scott, The Breeder's Handbook, 1957, pp. 1–76Handbook No. 4, National Chrysanthemum Society, Inc., U.S.A.

John Woolman, Chrysanthemums For Garden And Exhibition, 1953, pp. 1–103, W.H. & L Collingridge Ltd., Tavistock Street, London WC2 and Transatlantic Arts Incorporated, Forest Hills, New York.

H.G. Witham Fogg, Chrysanthemum Growing, 1962, pp. 1–171, John Gifford Limited, London, W.C.2.

National Agricultural Statistics Service, USDA Additional Floriculture Information, pp. 1–84, National Agricultural Statistics Service, Floriculture Crops, 1998 Summary, Jun. 1999.

Handbook on Chrysanthemum Classification, A publication of the Classification Committe National Chrysanthemum Society, Inc. U.S.A., 1996 Edition.

C. Ackerson, Chapter 12 Development of the Chrysanthemum in China, pp. 146–155, National Chrysanthemum Society Bulletin 1967.

C. Ackerson, Chapter 11 Original Species of the Chrysanthemum, pp. 105–107, National Chrysanthemum Society Bulletin 1967.

G.J. Dowrick, The Chromosomes of Chrysanthemum, I: The Species, pp. 365–375, Heredity 6:365–375, 1952.

* cited by examiner

*Primary Examiner*—Bruce R. Campell

*Assistant Examiner*—June Hwu

(74) *Attorney, Agent, or Firm*—Wood, Phillips, Katz, Clark & Mortimer

(57) ABSTRACT

A new and distinct Chrysanthemum plant named 'MN95-105-6' is provided.

4 Drawing Sheets

BACKGROUND OF THE INVENTION

The present invention comprises a new and distinctive chrysanthemum plant, hereinafter referred to by the cultivar name MN95-105-6. This new cultivar was the result of a cross in 1989 between *Chrysanthemum weyrichii* and *Chrysanthemum morifolium*. More specifically, the breeding program which resulted in the production of the new cultivar was carried out at St. Paul, Minn. The female or seed parent of 'MN95-105-6' was *Chrysanthemum weyrichii* 'Pink Bomb' (unpatented), commercially available from White Flower Farms, Conn. having the following characteristics: (a) the plant habit is prostrate and the plant spreads via rhizomes to form a large mat after the first year; (b) the plant dimensions are that the plant has a diameter of about 1.5' and is about 5–6" tall; (c) the plant is hardy in zones 4–9 (Southeast)/Zone 10 (west); (d) the flower of the plant is a single daisy, having light lavender-colored ray florets and central disc florets with yellow pollen; (e) the plant has leaves that are dark green in color, with a very shiny leaf surface (glossy), and glabrous leaf margins that are deeply incised; and (d) the plant tends to rosette, needs cold treatment to flower consistently, flowering can be sporadic with gaps in the plant architecture and the plant is an obligate short-day plant. The male or pollen parent of 'MN95-105-6' was either *Chrysanthemum morifolium* 'Crusader' or 'Adorn'. 'Crusader' (U.S. Plant Pat. No. 6,531) is a lavender daisy and is commercially available from Yoder Brothers, Inc., Barberton, Ohio and 'Adorn' (U.S. Plant Pat. No. 6,059) is a deep purple daisy and is commercially available from Pan American Seed Company, West Chicago, Ill. 'Crusader' and 'Adorn' having the following similar characteristics: (a) the plant habit is cushion; (b) the plant is hardy in zones 6–9 (Southeast)/Zone 10 (west); (c) the flower is a single daisy; (d) the plant has leaves that are similar to other Yoder Brother, Inc. cushion series chrysanthemums; and (c) the plant is a facultative short-day plant. Both 'Crusader' and 'Adorn' were each planted adjacent to the female parent. There were no other garden chrysanthemums within proximity for pollinators, such as bees, to use for pollen transfer. The resulting seeds, identified as 90-287-158 were collected. In 1990, a plant of 90-287-158 was crossed as the male parent with plants identified as 88-409-33, a University of Minnesota variety named 'Rose Blush' (unpatented), as the female parent and the resulting seeds, identified as cross number 91-204-2 were collected. In 1993, seedlings of the cross 91-204-2 were selfed and the resulting seeds, identified as 94-23-87 collected. In 1994, plants of 94-23-87 were selfed and the resulting seeds, identified as cross number 95-105 were collected. In 1995, seedlings of cross 95-105 were germinated and flowering progeny evaluated. 'MN95-105-6 was the sixth plant from the cross and was selected during the fall of 1995. 'MN95-105-6' is distinguishable from other varieties by its shrub-like growth in the second and successive years of growth, its superior winter hardiness, frost tolerance, and tendency to attract butterflies.

Asexual reproduction of the new cultivar by terminal or stem cuttings taken during 1996 through 1999 at St. Paul, Minn., U.S.A. has demonstrated that the characteristics of the new cultivar as herein described are firmly fixed and are retained through successive generations of such asexual propagation.

SUMMARY OF INVENTION

It was found that the cultivar of the present invention:

(a) exhibits extreme hybrid vigor, (b) develops, in its second and subsequent years after planting, when grown in the fall under natural day-length and without the application of growth regulators, into a flowering herbaceous shrub having a plant height of from about 1.9 to about 2.4 feet and a spread from about 2.5 to about 6.0 feet, (c) exhibits, in its second and subsequent years after planting and during the fall season (August–October), a massive floral display, (d) displays flowers which are slightly toned with grey, giving the flower petals a slightly altered coloration, (e) exhibits superior winter hardiness, including frost tolerance, and (f) exhibits self-pinching.

The 'MN95-105-6' cultivar has not been observed under all possible environmental conditions to date. Accordingly, it is possible that the phenotype may vary somewhat with variations in the environment, such as temperature, light intensity, and day length.

When the new cultivar of the present invention is compared to 'Jennifer' (U.S. Plant Pat. No. 8,987), it is found to exhibit a more spreading and prolific habit in its second and subsequent years after planting accompanied with a massive floral display. Reference is made to Table 1 below which compares certain characteristics of 'MN95-105-6' to 'Jennifer'.

TABLE 1

| Characteristic | 'MN95-105-6' | 'Jennifer' |
|---|---|---|
| Capitulum form and type | Triplex-quadriplex daisy | Flat decorative |
| Plant Height | About 14 to 19 inches (first year); about 2.4 to about 2.9 feet (second year) | 12 to 14 inches |
| Branching Pattern | Spreading and very prolific | Spreading |
| Flowering Response | 5.5 weeks | 7 weeks |
| Flower diameter | 6.3 cm | 6.4 to 7.3 cm |
| Ray florets, color, mature | Coral | Bronze with darker center |

BRIEF DESCRIPTION OF THE PHOTOGRAPHS

The accompanying photographs show as nearly true as it is reasonably possible to make the same in color illustrations of this type, typical flower and foliage characteristics of the new cultivar. The plants were grown in a greenhouse at St. Paul, Minn., U.S.A.

DETAILED BOTANICAL DESCRIPTION

Figure 1:
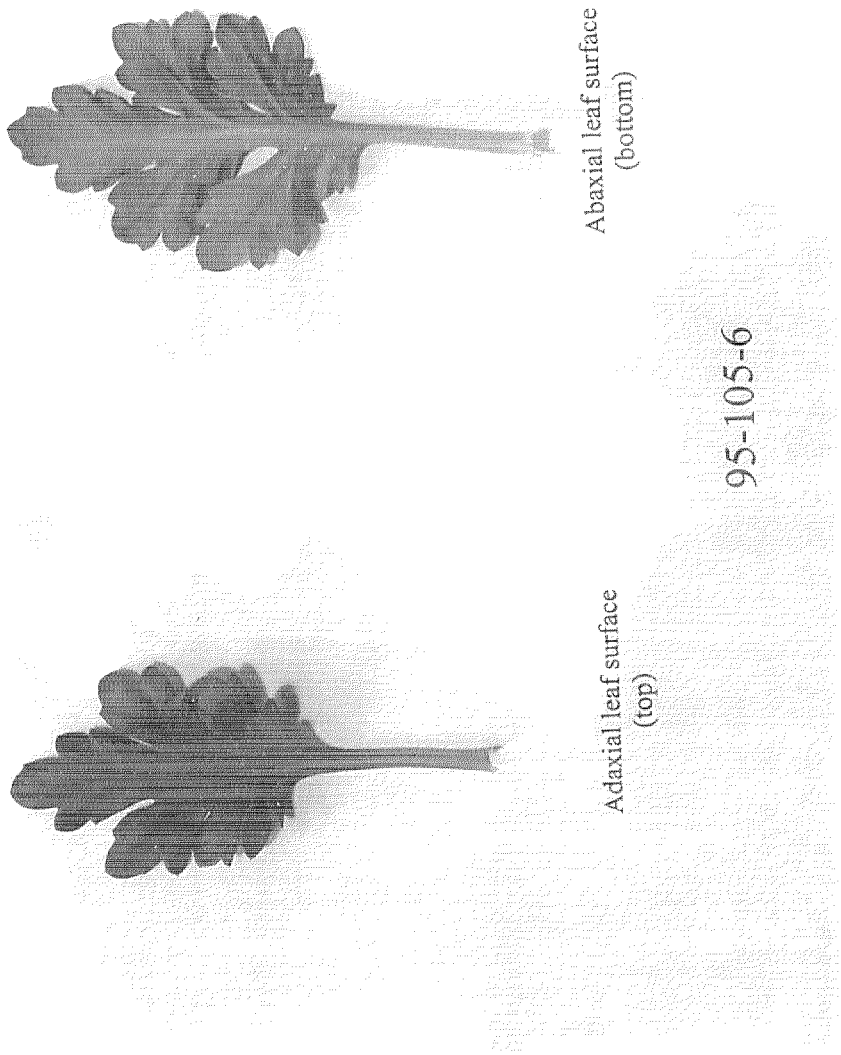
FIG. 1 shows an adaxial and abaxial views of the leaf shape of chrysanthemum variety 'MN95-105-6'.
Figure 2:
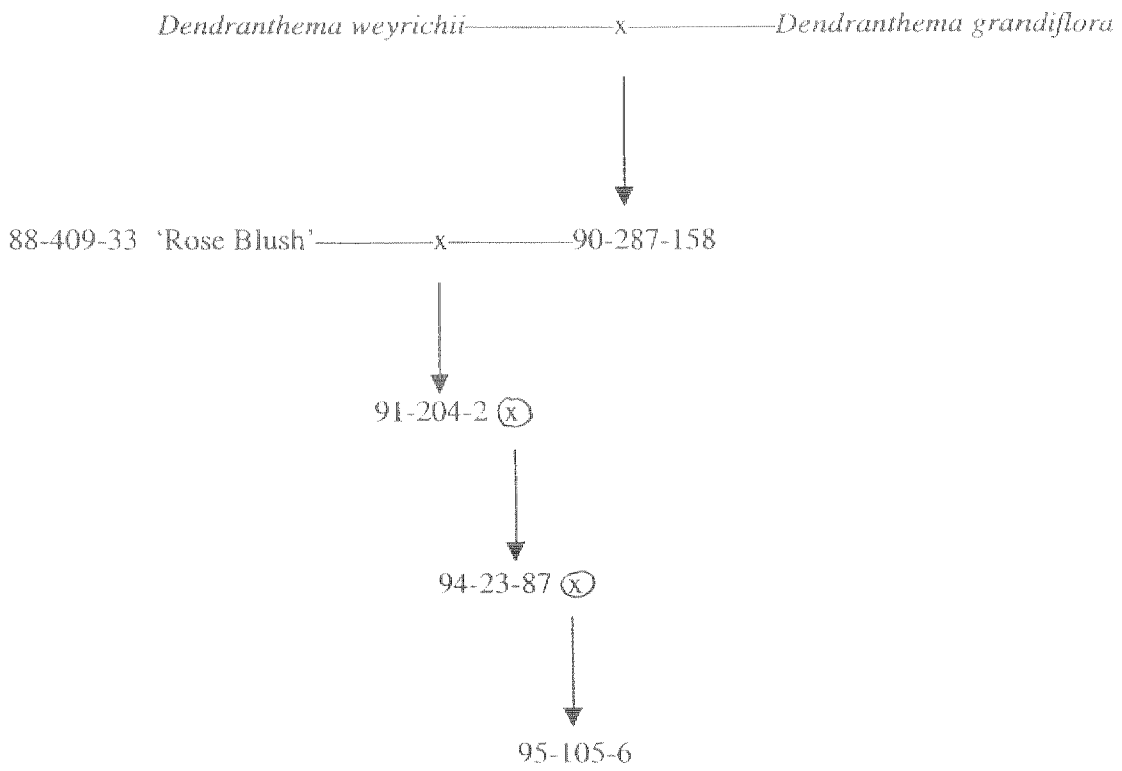
FIG. 2 shows the breeding history of chrysanthemum variety 'MN95-105-6'.
Figure 3:
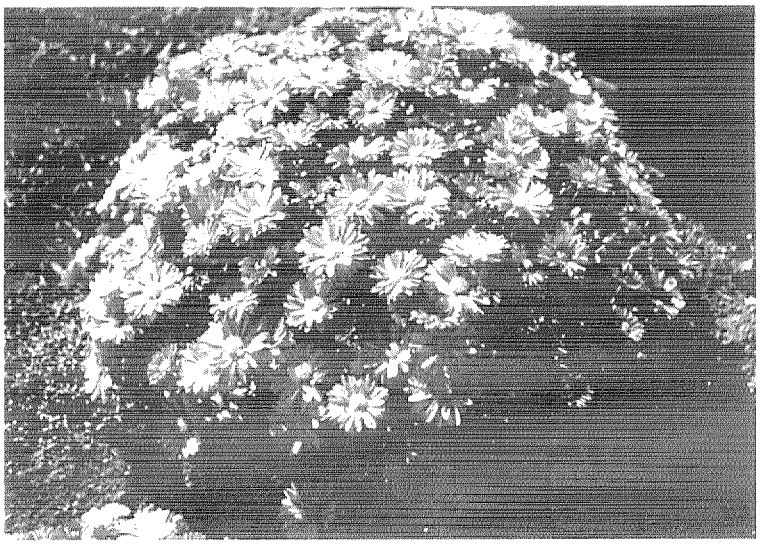
FIG. 3 is a color photograph of chrysanthemum variety 'MN95-105-6' after one year of growth.
Figure 4:
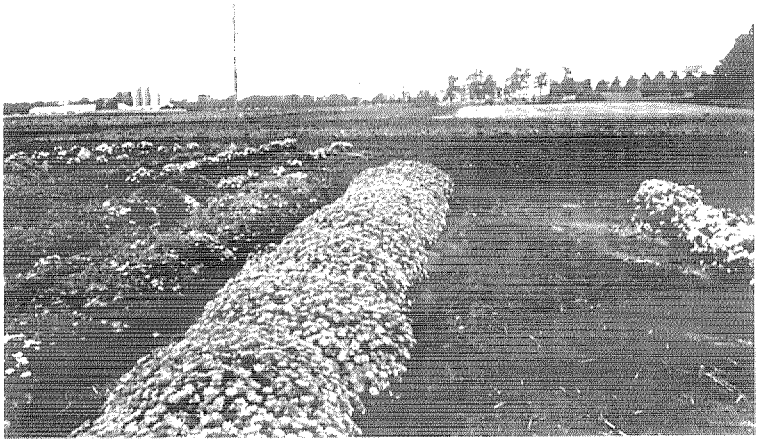
FIG. 4 is a color photograph of chrysanthemum variety 'MN95-105-6' after two years of growth.

The chart used in the identification of colors described herein is The R.H.S. Colour Chart of The Royal Horticultural Society, London, England. The color values were determined on Jan. 13, 2003, in St. Paul, Minn. The readings were taken between 11:00 a.m. and 1:00 p.m. under approximately 2500 footcandles of natural light. The plants were produced from cuttings taken from stock plants and were grown under greenhouse conditions comparable to those used in commercial practice while utilizing a soilless growth medium and maintaining temperatures of approximately 72° F. during the day and approximately 65° F. during the night.

Propagation:

*Type.*—Herbaceous stem cutting.

*Time to rooting.*—About 1 week.

*Rooting habit.*—Vigorous.

Botanical classification: Chrysanthemum hybrid 'MN95-105-6'.

Commercial classification: Chrysanthemum hybrid.

Plant description:

*Appearance, shape.*—Flattened mound (first year). Spherical mound (second year).

*Appearance, growth habit.*—Mound.

*Appearance, growth rate/vigor.*—Vigorous.

*Plant height.*—About 14 to about 19 inches (first year) about 1.9 to about 2.4 feet (second year).

*Lateral branch length.*—1 to 3 feet.

*Quantity of lateral branches after removal of apical meristem.*—One per node.

*Stem color.*—RHS Green Group 139B.

Foliage description:

*Number of leaves per plant.*—Greater than 10,000 (second year).

*Number of leaves per lateral branch.*—5 to 25.

*Leaf arrangement.*—Alternate.

*Leaf size, fully expanded, length.*—9.7 cm.

*Leaf size, fully expanded, width.*—4.6 cm.

*Leaf apex.*—Obtuse to mucronate.

*Leaf base.*—Cuneate to oblique.

*Leaf margin.*—Incised (Mulberry-like incisions).

*Leaf texture.*—Glabrous.

*Petiole length.*—3.8 cm.

*Color, young foliage adaxial surface.*—RHS Green Group 138B.

*Color, young foliage abaxial surface.*—RHS Green Group 138D.

*Color, fully expanded foliage adaxial surface.*—RHS Green Group 138A.

*Color, fully expanded foliage abaxial surface.*—RHS Green Group 138C.

*Color, venation adaxial surface.*—RHS Green Group 128D.

*Color, venation abaxial surface.*—RHS Green Group 128D.

*Color, petiole.*—RHS Green Group 139B.

Phyllary description:

*Appearance.*—The involucral bracts (phyllaries) are crenulate.

*Color.*—RHS Green Group 139C.

*Texture.*—Glabrous.

*Size.*—Approximately 0.2–0.4 cm in length.

Inflorescence description:

*Appearance.*—Head (composite), triplex-quadriplex daisy.

*Flowering response.*—About 5.5 weeks (SD).

*Quantity of inflorescences.*—About 800 (first year). About 6,000 (second year).

*Inflorescence size, diameter.*—6.3 cm.

*Inflorescence size, depth (height).*—2.3 cm.

*Inflorescence size, diameter of disc.*—1.5 cm.

*Opening inflorescences, bud shape.*—Flattened hemisphere to widened upright tubular.

*Opening inflorescences, bud size, length.*—0.7 cm.

*Opening inflorescences, bud size, width.*—0.9 cm.

*Opening inflorescences, bud color.*—RHS Red-Purple Group 74A.

*Ray florets, shape.*—Linear lanceolate.

*Ray florets, size, length.*—3 cm.

*Ray florets, size, width.*—0.7 cm.

*Ray florets, apex.*—Multi-notched mucronulate.

*Ray florets, base.*—Attenuate.

*Ray florets, margin.*—Entire.

*Ray florets, texture.*—Glabrous.

*Ray florets, aspect.*—From about 45° vertical to slightly pendant 45°.

*Number of ray florets per inflorescence.*—About 60.

*Ray florets, color, when opening, adaxial surface.*—RHS Red-Purple Group 74B.

*Ray florets, color, when opening, abaxial surface.*—RHS Red Group 43C.

*Ray florets, color, mature adaxial surface.*—RHS Orange-Red Group 35C.

*Ray florets, color, mature, abaxial surface.*—RHS Orange-Red Group 35D.

*Ray florets, color, fading to.*—RHS Red Group 39B.

*Disc florets, shape.*—Tubular, rounded at tip.

*Disc florets, size, length.*—0.6 cm.

*Disc florets, size, width.*—0.4 cm.

*Number of disc florets per inflorescence.*—About 191.

*Disc florets, color, immature.*—RHS Yellow-Orange Group 16A.

*Disc florets, color, mature.*—RHS Yellow-Orange Group 15A with an eye in the center of each disc which is RHS Red Group 46B.

*Peduncle, aspect, strength.*—Stiff.

*Peduncle, aspect, angle to stem.*—30°.

*Peduncle, length, first peduncle.*—4.2 cm.

*Peduncle, length, fourth peduncle.*—7 cm.

*Peduncle, texture.*—Slightly hirsute.

*Peduncle, color.*—RHS Green Group 138B.

*Reproductive organs, androecium, floret location.*—Disc florets.

*Anther color.*—RHS Yellow-Orange Group 21B.

*Pollen, abundance.*—Abundant.

*Pollen, color.*—RHS Yellow-Orange Group 21B.

*Reproductive organs, gynoecium, floret location.*—Disc/ray florets.

*Style color.*—RHS Yellow-Orange Group 7B.

*Stamen description.*—Stamens are located within each individual disc floret. Each stamen is borne on a filament that, when mature (dehiscent with pollen shedding longitudinally along the long axis of the anther), places the stamens above the stigma (i.e. the top portion of the pistil).

*Pistil number.*—Each ray floret possesses one pistil (there are approximately 60 per inflorescence). Likewise, each disk floret also possesses a pistil (there are approximately 191 per inflorescence). Therefore, the total number of pistils/inflorescence is 251 (60+191). The size of the pistil (length) is approximately 1 cm.

Disease resistance: None Known as 'MN95-105-6' has not been tested for any diseases.

Seed production and fruit: About 251 ovules/flower. The fruit is an achene, a small, dry, indehiscent fruit with a single locule and a single seed, and with the seed attached to the ovary wall at a single point. The achene does not have any pappus of awns or bristles; its general shape is a half-inflated football (oval with pointed ends). Seed Size is about 0.2–0.5 cm in length and about 0.1–0.2 cm in width. The surface texture is ridged. The color designation for the seed is RHS Brown Group 200D.

Winter hardiness: Hardy in zones 3–10 in uncovered field conditions without the need for added protection such as snow fences, mulch, etc.

Frost tolerance: Yes, extends blooming season to the first freeze in the north (In zones 3–4 the first frost usually takes place between September 1–15. In zones 3–4, the first freeze usually takes place between October 1–20).

Fragrance: Fragrance is noticeable when handling or bruising the foliage.

Longevity of the bloom: Flower longevity is temperature dependent. Under normal conditions in the field during the fall season, flowers will typically last about 2–4 plus weeks.

What is claimed is:

1. A new and distinct Chrysanthemum plant named 'MN95-105-6' as herein described and illustrated.

* * * * *